(12) United States Patent
Rodriguez San Juan et al.

(10) Patent No.: US 12,274,862 B2
(45) Date of Patent: Apr. 15, 2025

(54) SELF-CONTROLLABLE LOAD SPRING WASHER

(71) Applicant: Becton, Dickinson and Company, Franklin Lakes, NJ (US)

(72) Inventors: Nestor Rodriguez San Juan, Hamburg, NJ (US); Evan Leibowitz, Linden, NJ (US); Kayla Kaspar, Parsippany, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 797 days.

(21) Appl. No.: 16/922,137

(22) Filed: Jul. 7, 2020

(65) Prior Publication Data

US 2021/0008282 A1    Jan. 14, 2021

Related U.S. Application Data

(60) Provisional application No. 62/872,017, filed on Jul. 9, 2019.

(51) Int. Cl.
*A61M 5/20* (2006.01)
*A61M 5/24* (2006.01)
*B21D 53/22* (2006.01)
*C08L 23/16* (2006.01)

(52) U.S. Cl.
CPC ........ *A61M 5/2033* (2013.01); *A61M 5/2053* (2013.01); *B21D 53/22* (2013.01); *C08L 23/16* (2013.01); *A61M 2005/2477* (2013.01); *A61M 2205/02* (2013.01)

(58) Field of Classification Search
CPC .. A61M 39/165; A61M 39/162; A61M 39/16; A61M 39/20; A61M 2205/02; A61M 2005/3104; A61M 5/2033; A61M 5/2053; F16F 1/03

See application file for complete search history.

(56) References Cited

U.S. PATENT DOCUMENTS

| 3,730,509 | A | * | 5/1973 | Jorn | F16F 1/428 |
| | | | | | 267/152 |
| 4,892,517 | A | * | 1/1990 | Yuan | A61M 1/062 |
| | | | | | 604/74 |
| 5,505,704 | A | | 4/1996 | Pawelka et al. | |
| 6,413,237 | B1 | | 7/2002 | Caizza et al. | |
| 6,517,060 | B1 | * | 2/2003 | Kemeny | F16F 1/32 |
| | | | | | 267/136 |
| 8,795,239 | B2 | | 8/2014 | Plumptre | |
| 8,845,254 | B2 | * | 9/2014 | Lee | F16B 39/282 |
| | | | | | 411/165 |
| 9,358,344 | B2 | | 6/2016 | Pala | |

(Continued)

FOREIGN PATENT DOCUMENTS

| CN | 1356148 A | 7/2002 |
| CN | 103648556 A | 3/2014 |

(Continued)

*Primary Examiner* — Michael J Tsai
*Assistant Examiner* — Neeraja Gollamudi
(74) *Attorney, Agent, or Firm* — The Webb Law Firm

(57) ABSTRACT

Provided herein is a load spring washer configured for use with a medical injection device, having a main body having a proximal surface and a distal surface and one or more protrusions extending proximally away from the proximal surface of the main body.

9 Claims, 20 Drawing Sheets

(56) References Cited

U.S. PATENT DOCUMENTS

| | | | |
|---|---|---|---|
| 9,421,334 B2 | 8/2016 | Quinn et al. | |
| 2007/0021718 A1* | 1/2007 | Burren | G01F 11/027 604/110 |
| 2008/0195057 A1 | 8/2008 | Graf et al. | |
| 2011/0306939 A1* | 12/2011 | Harms | A61M 5/24 29/446 |
| 2012/0104120 A1* | 5/2012 | Holt | F16F 1/328 239/533.2 |
| 2014/0094765 A1 | 4/2014 | Pala | |
| 2015/0273151 A1* | 10/2015 | McLoughlin | A61M 5/002 604/66 |
| 2016/0193414 A1 | 7/2016 | McLoughlin et al. | |
| 2017/0312441 A1 | 11/2017 | Draper et al. | |
| 2017/0348489 A1 | 12/2017 | Hirschel et al. | |
| 2018/0221563 A1 | 8/2018 | Frederiksen et al. | |
| 2019/0038842 A1 | 2/2019 | Pedersen et al. | |

FOREIGN PATENT DOCUMENTS

| | | | |
|---|---|---|---|
| DE | 4115002 A1 | 12/1991 | |
| EP | 0692988 B1 | 8/1997 | |
| GB | 2068494 A | 8/1981 | |
| JP | 200231120 A | 1/2002 | |
| JP | 2002291724 A | 10/2002 | |
| JP | 2014519892 A | 8/2014 | |
| WO | WO-2004027274 A1 * | 4/2004 | F16F 1/32 |
| WO | 2010043533 A1 | 4/2010 | |
| WO | 2012125876 A1 | 9/2012 | |

\* cited by examiner

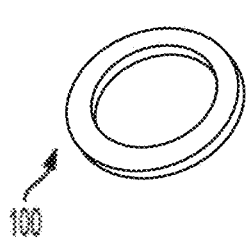 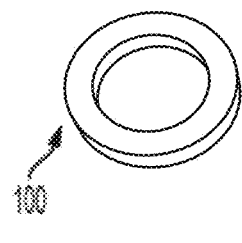 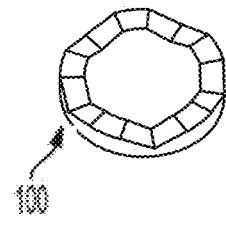
FIG. 11A  FIG. 11B  FIG. 11C
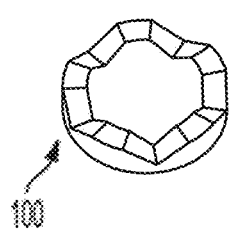 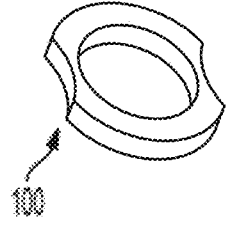
FIG. 11D  FIG. 11E

SELF-CONTROLLABLE LOAD SPRING WASHER

CROSS-REFERENCE TO RELATED APPLICATIONS

The present application claims the benefit of U.S. Provisional Patent Application No. 62/872,017, filed Jul. 9, 2019, the content of which is incorporated herein by reference in its entirety.

BACKGROUND OF THE INVENTION

Field of the Invention

The present disclosure relates generally to spring washers useful as replacements for helical coil springs for medical devices, and, in particular embodiments or aspects, to injection devices including spring washers, including elastomeric spring washers.

Description of Related Art

Medical injection devices often utilize resilient members, such as springs, placed between various components, to bias the components in order to ensure more accurate drug delivery. However, there are shortcomings to the use of current resilient members used in medical injection devices, such as a lack of control and load recovery. Accordingly, there is a need in the art for a more robust component to allow for greater load recovery.

SUMMARY OF THE INVENTION

Provided herein is a load spring washer configured for use with a medical injection device, having a main body having a proximal surface and a distal surface; and one or more protrusions extending proximally away from the proximal surface of the main body.

Also provided herein is a load spring washer configured for use with a medical injection device, having a circular main body having a proximal surface and a distal surface, wherein a cross-sectional profile of the main body taken along a plane extending between the proximal surface and the distal surface has a sinusoidal shape.

Also provided herein is a load spring washer configured for use with a medical injection device, having a circular main body having a frustoconical shape.

Also provided herein is a load spring washer configured for use with a medical injection device, having a main body comprising a ring having a proximal surface and a distal surface, the load spring washer comprising at least one arm and/or one flange projecting parallel to a longitudinal axis defined by the proximal surface and distal surface of the main body.

Also provided herein is a medical injection device having a housing; a brake member received within the housing; a cartridge received within the housing and holding a composition therein; a load spring washer as described herein, received within the housing and positioned between the brake member and the housing; an injection needle in fluid communication with the cartridge; and an actuation member at a proximal end of the housing, the actuation member configured to actuate the medical injection device to deliver the composition through the injection needle.

Further embodiments or aspects are set forth in the following numbered clauses:

1. A load spring washer configured for use with a medical injection device, comprising: a main body having a proximal surface and a distal surface; and one or more protrusions extending proximally away from the proximal surface of the main body.

2. The load spring washer of clause 1, wherein the main body is substantially circular.

3. The load spring washer of clause 1 or clause 2, wherein the main body defines an aperture, such that the main body is ring shaped.

4. The load spring washer of any of clauses 1-3, wherein a cross-sectional profile of the one or more protrusions taken along a plane extending between the proximal surface and the distal surface comprises a parallelogram.

5. The load spring washer of any of clauses 1-3, wherein the one or more protrusions have a cylindrical shape.

6. The load spring washer of clause 5, wherein a cross-sectional profile of the one or more protrusions taken along a plane extending between the proximal surface and the distal surface comprises a cylindrical shape.

7. The load spring washer of clause 5 or clause 6, wherein the cylindrical shape defines a hollow interior.

8. The load spring washer of clause 7, wherein the hollow interior is filled with a gas.

9. The load spring washer of clause 7, wherein the hollow interior comprises a vacuum.

10. The load spring washer of any of clauses 1-3, wherein a cross-sectional profile of the one or more protrusions taken along a plane extending between the proximal surface and the distal surface comprises a rhomboid.

11. The load spring washer of any of clauses 1-3, wherein a cross-sectional profile of the one or more protrusions taken along a plane extending between the proximal surface and the distal surface comprises an s-shape.

12. The load spring washer of any of clauses 1-3, wherein a cross-sectional profile of the one or more protrusions taken along a plane extending between the proximal surface and the distal surface comprises an 1-shape.

13. The load spring washer of any of clauses 1-3, wherein the main body comprises a plurality of rings.

14. The load spring washer of clause 13, wherein the plurality of rings comprise concentric circles, with a gap between each of the concentric circles.

15. The load spring washer of clause 14, wherein at least one of the concentric circles has a width that is greater than a width of another of the concentric circles.

16. The load spring washer of any of clauses 13-15, wherein a cross-sectional profile of the one or more protrusions taken along a plane extending between the proximal surface and the distal surface comprises a u-shape, wherein the u-shape comprises: a first arm connected to a first of the plurality of rings of the main body and a second arm connected to a second of the plurality of rings of the main body, both the first arm and the second arm extending parallel to a longitudinal axis defined by the proximal surface and the distal surface of the main body; and a cross-member connected to the first arm and the second arm and extending perpendicular to the longitudinal axis defined by the proximal surface and the distal surface of the main body.

17. The load spring washer of any of clauses 13-15, wherein the one or more protrusions comprise an arch comprising: a first arm connected to a first of the plurality of rings of the main body and a second arm connected to a second of the plurality of rings of the main body, both the first arm and the second arm extending parallel to a longitudinal axis defined by the proximal surface and the distal surface of the main body; and a curved portion connected to the first arm and the second arm.

18. The load spring washer of any of clauses 1-3, wherein the protrusion comprises a frustoconical portion.

19. The load spring washer of any of clauses 1-18, wherein the load spring washer comprises an elastomeric material.

20. The load spring washer of any of clauses 1-19, wherein the load spring washer comprises a rubber.

21. The load spring washer of any of clauses 1-20, wherein the load spring washer is formed of an ethylene propylene diene monomer rubber.

22. The load spring washer of any of clauses 1-21, wherein a Shore A hardness of the load spring washer is 20-40, preferably 30-40.

23. A load spring washer comprising a circular main body having a proximal surface and a distal surface, wherein a cross-sectional profile of the main body taken along a plane extending between the proximal surface and the distal surface comprises a sinusoidal shape.

24. A load spring washer comprising a circular main body having a frustoconical shape.

25. A load spring washer comprising a main body comprising a ring having a proximal surface and a distal surface, the load spring washer comprising at least one arm and/or one flange projecting parallel to a longitudinal axis defined by the proximal surface and distal surface of the main body.

26. The load spring washer of any of clauses 23-25, wherein the load spring washer comprises an elastomeric material.

27. The load spring washer of any of clauses 23-26, wherein the load spring washer comprises a rubber.

28. The load spring washer of any of clauses 23-27, wherein the load spring washer is formed of an ethylene propylene diene monomer rubber.

29. The load spring washer of any of clauses 23-28, wherein a Shore A hardness of the load spring washer is 20-40, preferably 30-40.

30. A medical injection device comprising a housing; a brake member received within the housing; a cartridge received within the housing and holding a composition therein; a load spring washer according to any of clauses 1-29, received within the housing and positioned between the brake member and the housing; an injection needle in fluid communication with the cartridge; and an actuation member at a proximal end of the housing, the actuation member configured to actuate the medical injection device to deliver the composition through the injection needle.

BRIEF DESCRIPTION OF THE DRAWINGS

FIGS. 11A-11E show various embodiments or aspects of a load spring washer as described herein;

DESCRIPTION OF THE INVENTION

Figure 1A:
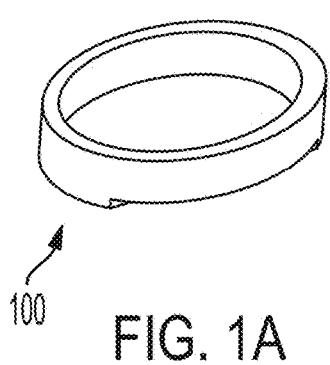
FIGS. 1A-1C show various embodiments or aspects of a load spring washer as described herein.

The use of numerical values in the various ranges specified in this application, unless expressly indicated otherwise, are stated as approximations as though the minimum and maximum values within the stated ranges are both preceded by the word "about". As used herein, the term "about" means the stated value ±10%. In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

The figures accompanying this application are representative in nature, and should not be construed as implying any particular scale or directionality, unless otherwise indicated. For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. Hence, specific dimensions and other physical characteristics related to the embodiments disclosed herein are not to be considered as limiting.

Provided herein is a load spring washer for use as a replacement for a spring in a medical device. A spring washer, as is known to those of skill in the art, is a washer having axial flexibility. As used herein, the "spring" aspect of a spring washer for use in a medical device is a washer that has axial flexibility by virtue of the material from which the washer is formed (e.g., compressibility/expandability derived from the elastomeric nature of materials), by virtue of a shape or form of the washer, and combinations thereof. In non-limiting embodiments or aspects, the load spring washer is formed of an elastomeric material. In non-limiting embodiments or aspects, the elastomeric material is a highly resilient elastomeric material. In non-limiting embodiments or aspects, the load spring washer is formed of a rubber. In non-limiting embodiments or aspects, the rubber is polyisoprene rubber, silicone rubber, and/or butyl rubber. In non-limiting embodiments or aspects, the rubber is butyl rubber (IIR), isoprene rubber (IR), butadiene rubber (BR), styrene-butadiene rubber (SBR), ethylene-propylene rubber (EPM), ethylene-propylene-diene rubber (EPDM), chlorosulphonated polyethylene (CSM), ethylene-vinyl acetate copolymer (EVA), styrene-isoprene rubber (SIR), thermoplastic elastomers, and/or natural rubbers.

In non-limiting embodiments or aspects, the load spring washer is formed of a elastomeric copolymer, including, without limitation, thermoplastic elastomers, thermoplastic vulcanizates, styrene copolymers such as styrene-butadiene (SBR or SBS) copolymers, styrene-isoprene (SIS) block polymers or styrene-isoprene/butadiene (SIBS), in which the content of styrene in the styrene block copolymer ranges from about 10% to about 70%, and preferably from about 20% to about 50%. The elastomer composition can include, without limitation, antioxidants and/or inorganic reinforcing agents to preserve the stability of the elastomer composition, a vulcanizing agent, a vulcanizing accelerator, a vulcanizing activator, a processing aid, a filler, etc. to maintain and improve the physical properties and heat resistance of the rubber material.

In non-limiting embodiments or aspects, the load spring washer is formed of a material having a Shore A value of 20-40 optionally 30-40, all values and subranges therebetween inclusive. In non-limiting embodiments or aspects, the load spring washer is formed of a material comprising an ethylene propylene diene monomer (EPDM) rubber. In non-limiting embodiments or aspects, the load spring washer is formed of a material comprising an EPDM rubber, and various fillers/additives. In non-limiting embodiments or aspects, the load spring washer is formed of an ultra-high molecular weight EPDM rubber (e.g., KELTAN 9565Q), various fillers (e.g., MISTRON Vapor), mineral oil, zinc oxide, stearic acid, antioxidant(s) (e.g., SONGNOX 1076), curing accelerator(s) (e.g., TBzTD), vulcanizing agent(s) (e.g., VULTAC 710), and sulfur (such as a wettable sulfur).

In non-limiting embodiments or aspects, the load spring washer is formed of a foam. In non-limiting embodiments or aspects, the load spring washer is formed of a mixture of materials, for example, and without limitation, a metal and/or polymer, together with a rubber and/or foam. For example, and without limitation, a load spring washer as described below can include a main body that is a metal, a polymer, or a mix, together with a protrusion that is formed of an elastomeric material, such as a rubber, foam, or elastomeric polymer.

Figure 1B:
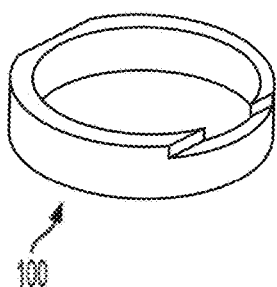
Figure 1C:
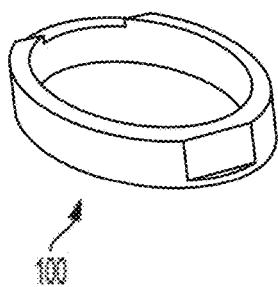

Turning to FIGS. 1A-1C, shown are various load spring washers 100 as described herein. The load spring washers shown in FIGS. 1A-1C are substantially circular; however, those of ordinary skill in the art will appreciate that any suitable shape can be used, depending on the intended use/application. FIGS. 11A-11E show various non-limiting embodiments or aspects of shapes that can be utilized for load spring washers 100 as described herein, including a circular, ring shape, a star shape, and an H-shape. FIGS. 11A-11B show non-limiting embodiments or aspects of a ring shape, FIGS. 11C-11D show non-limiting embodiments or aspects of a star shape, and FIG. 11E shows a non-limiting embodiment or aspects of an H-shape, that can be utilized for load spring washers 100 as described herein. It is to be understood that the illustrated shapes are merely exemplary, and that the present disclosure is not so limited.

Figure 2:
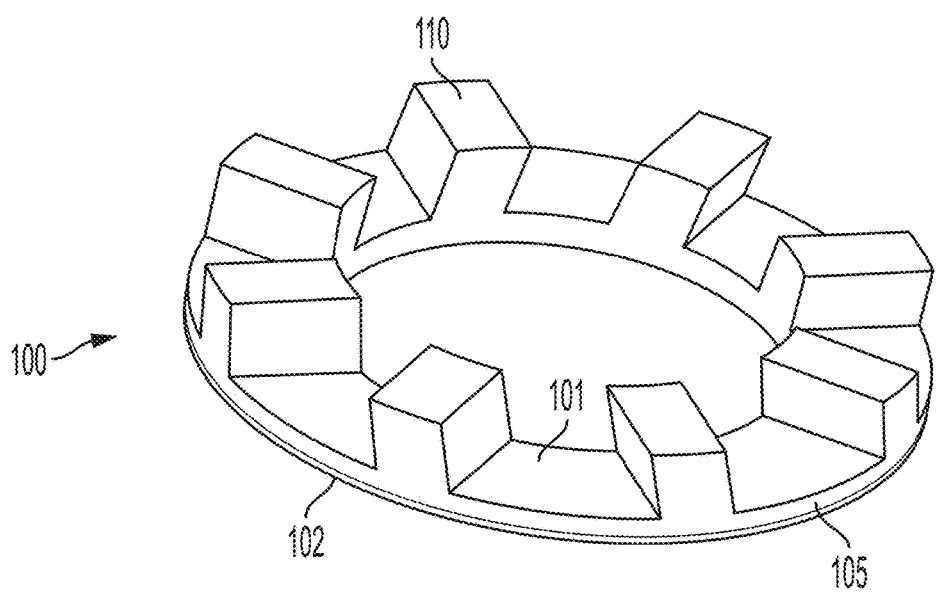
FIG. 2 shows a schematic image of a load spring washer according to one non-limiting embodiment or aspect.

Turning to FIG. 2, shown is a schematic view of a load spring washer 100 according to a non-limiting embodiment or aspect. In non-limiting embodiments or aspects, load spring washer 100 can include a main body 105 and one or more protrusions 110, such as pillars, extending from the main body 105. Main body includes proximal surface 101 and distal surface 102, defining a longitudinal axis therebetween. Without wishing to be bound by the theory, it is believed that pillars 110 allow for modification of the compressive force of the load spring washer by providing resistance to compression. While FIG. 2 (and other figures) show specific numbers of protrusions, such as pillars, it is to be understood that the number of protrusions, such as pillars 110, can be modified to provide appropriate modification of compressive forces for intended applications. Protrusions 110 may assume any useful shape and orientation on the load spring washer main body 105. Those of skill in the art will appreciate that the thickness (depth) and circumferential size (width) of the main body 105 can be adjusted, so long as the load spring washer exhibits the characteristics described herein in terms of flex, or buckling when force or pressure is applied parallel to the longitudinal axis defined by the proximal surface 101 and distal surface 102 of the main body 105.

Figure 3A:
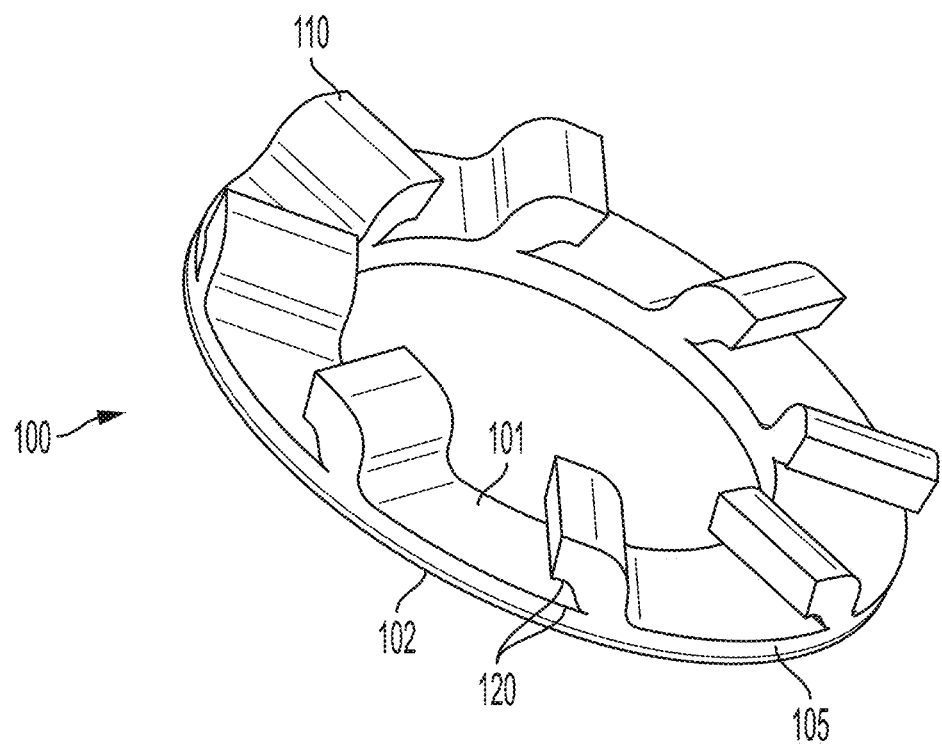
FIGS. 3A-3B show a schematic image of a load spring washer according to one non-limiting embodiment or aspect and a force diagram showing flexing of the pillars of the load spring washer.
Figure 3B:
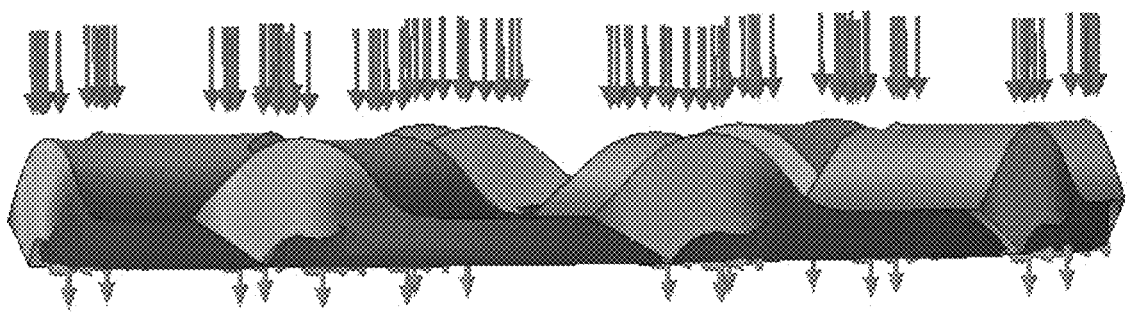

Turning to FIG. 3A, shown is a schematic view of a load spring washer 100 according to a non-limiting embodiment or aspect. Load spring washer 100 includes main body 105 and one or more s-shaped protrusions 110, with a gap 120 between the proximal (uppermost) portion of the s-shaped protrusion and the main body 105 having a predetermined height. The design of protrusions 110 in FIG. 3 allows for the protrusions to, when force is applied in a direction perpendicular to the main body 105, flex or buckle to a flat orientation, as shown in FIG. 3B, such that the height of gap 120 is smaller than when no force is applied to the load spring washer 100. As noted above, protrusions, here s-shaped protrusions, including individual portions thereof, can be of any suitable size, and gap 120 may similarly be of any suitable size.

Figure 4A:
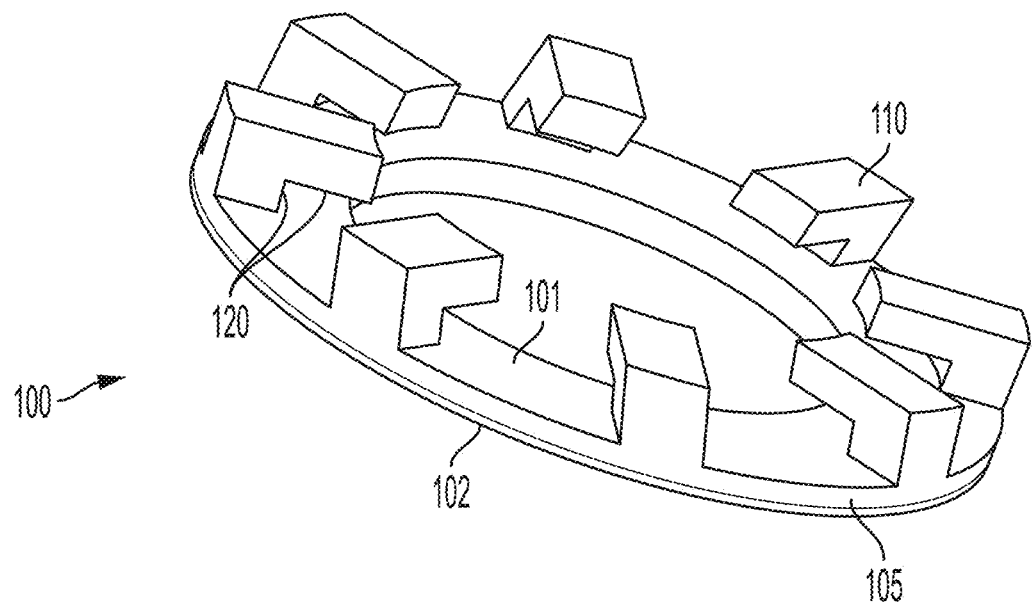
FIGS. 4A-4B show schematic images of a load spring washer according to non-limiting embodiments or aspects.
Figure 4B:
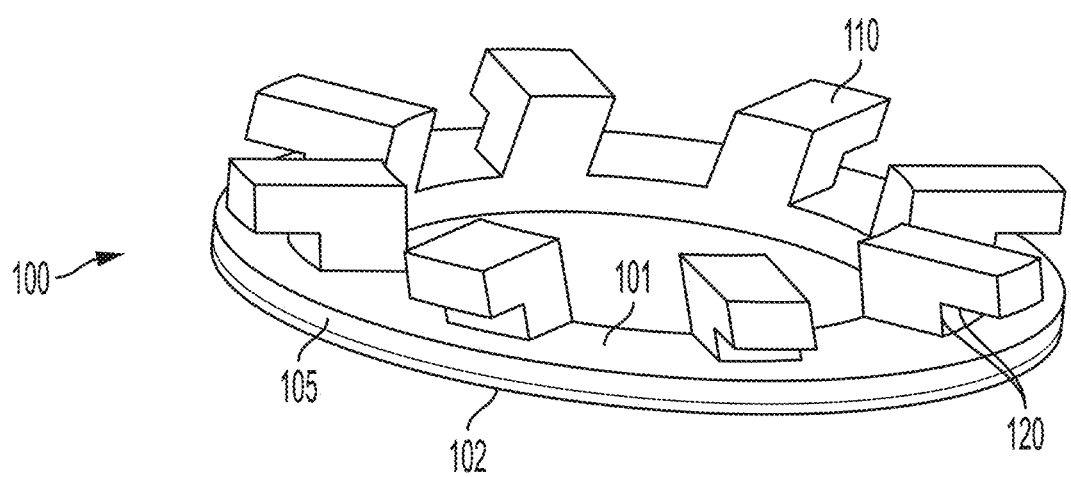

Turning to FIGS. 4A-4B, shown is a schematic view of a load spring washer 100 according to a non-limiting embodiment or aspect. Load spring washer 100 includes main body 105 and one or more 1-shaped protrusions 110, with a gap 120 between the proximal (uppermost) portion of the 1-shaped protrusion 110 and the main body 105. As noted above, protrusions, here 1-shaped protrusions, including individual portions thereof, can be of any suitable size, and gap 120 may similarly be of any suitable size.

Figure 5:
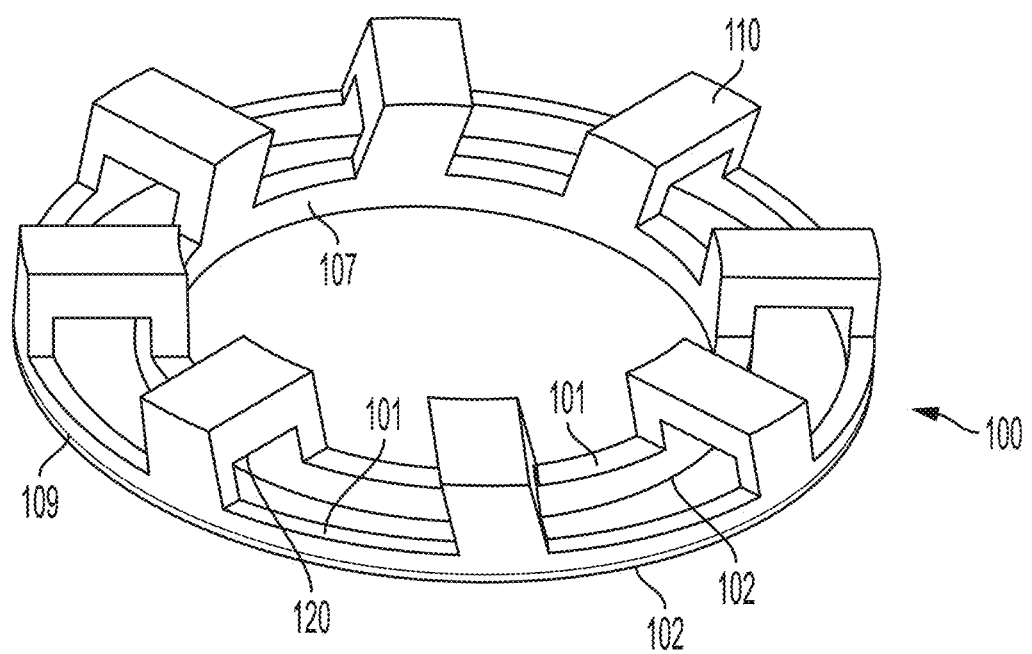
FIG. 5 shows a schematic image of a load spring washer according to one non-limiting embodiment or aspect.
Figure 6A:
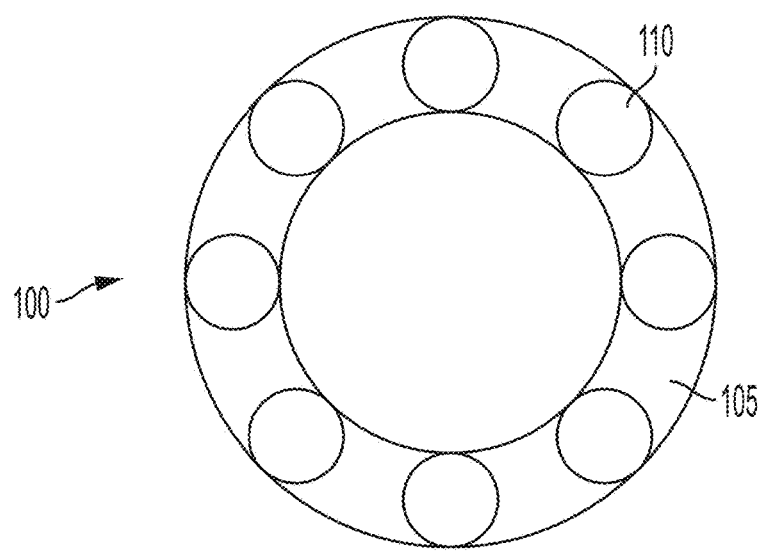
FIGS. 6A-6D show schematic images of a load spring washer according to non-limiting embodiments or aspects.
Figure 6B:
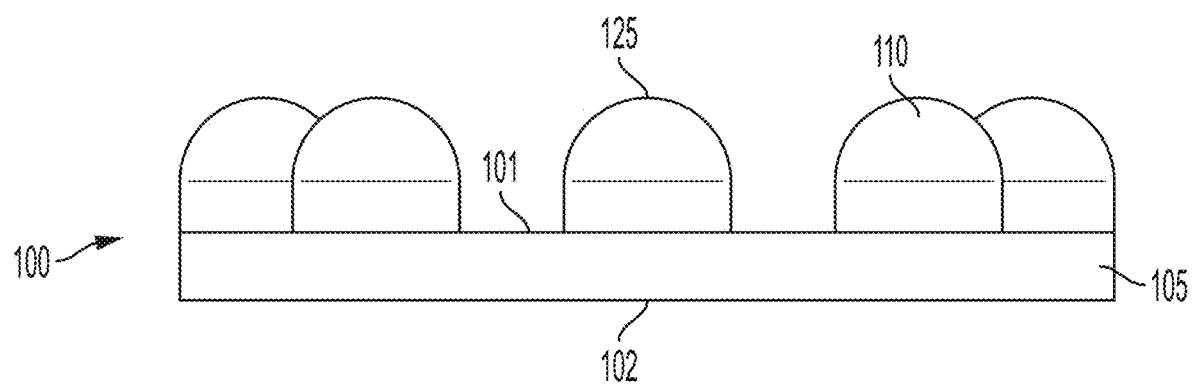
Figure 6C:
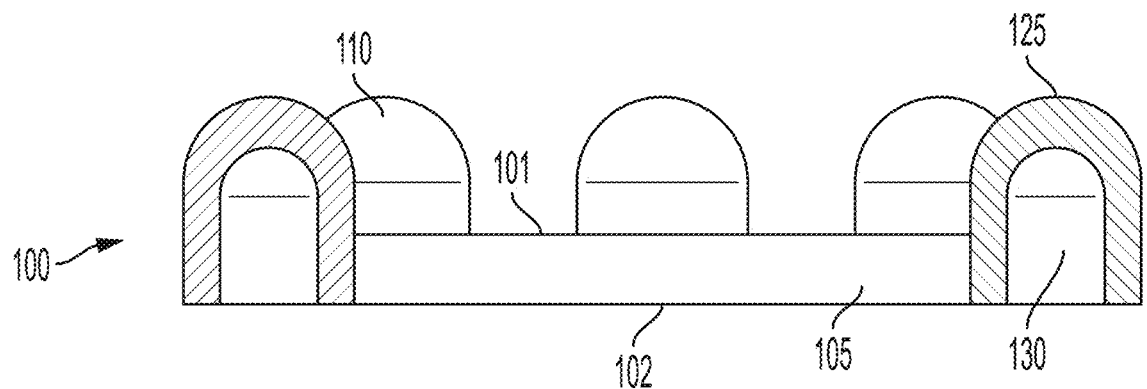
Figure 6D:
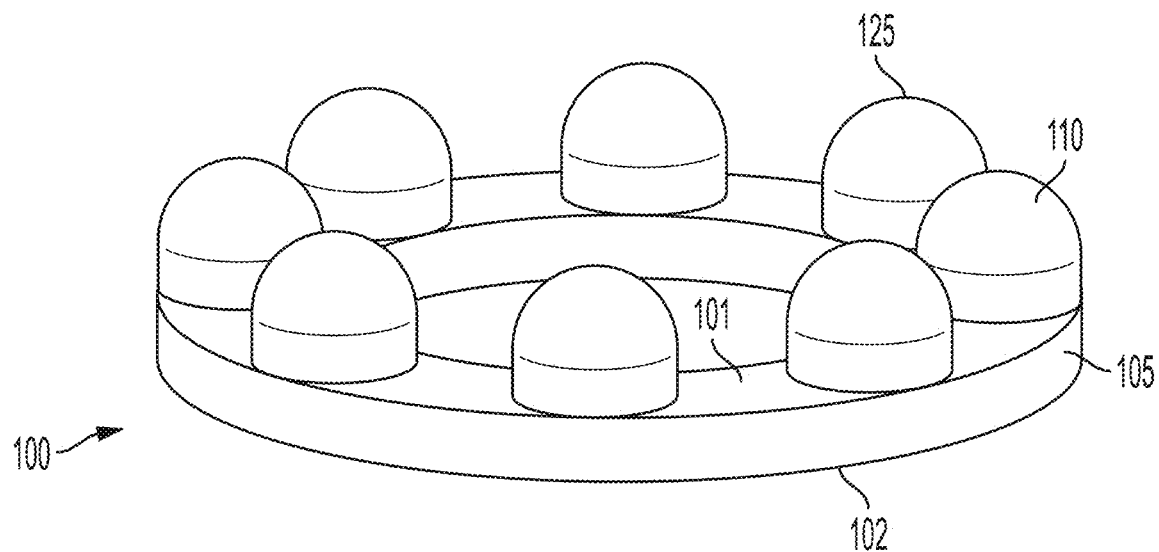

Turning to FIG. 5, shown is a schematic view of a load spring washer 100 according to a non-limiting embodiment or aspect. Load spring washer 100 includes a multi-piece main body, including an inner portion 107 and an outer portion 109. In non-limiting embodiments or aspects, inner portion 107 and outer portion 109 are at least two concentric circles. In non-limiting embodiments or aspects, at least one of the concentric circles has a width that is greater than a width of another of the concentric circles. Lock spring washer 100 further includes one or more protrusions 110. In the illustrated embodiment or aspect, protrusion includes a proximal (uppermost) end and a distal (bottommost) end, and the protrusion 110 bridges the inner 107 and outer 109 portions of the main body, with a gap 120 between the proximal end of the protrusion 110 and the inner 107 and outer 109 portions of the main body. Protrusions 110 have a rectangular shape in FIG. 5; however, the present disclosure is not so limited, and the protrusions 100 may assume any useful shape or orientation, such as, for example and without limitation an arc or arch shape.

Turning to FIGS. 6A-6D, shown are schematic top (FIG. 6A), side (FIG. 6B), cross-sectional (FIG. 6C), and perspective views (FIG. 6D) of a load spring washer 100 according to a non-limiting embodiment or aspect. Load spring washer 100 includes a main body 105 and protrusion 110. In the illustrated non-limiting embodiment or aspect, protrusion has a cylindrical shape, optionally with a dome 125 at a proximal (uppermost) end. In non-limiting embodiments or aspects, interior of cylinder may be hollow, defining a chamber 130. The presence of chamber 130, which may be subject to vacuum during manufacture such that no air is present therein, allows for the dome (120) and/or the walls of protrusion 110 to collapse, or buckle, inward towards the distal (bottommost) end of the load spring washer 100 when force is applied to the load spring washer 110 in a direction parallel to the longitudinal axis defined by proximal surface 101 and distal surface 102 of main body 105. In non-limiting embodiments or aspects, outermost circumference of main body 105 can include one or more protrusions to provide greater frictional engagement between the outer diameter of main body 105 and the inner diameter of a medical device housing into which the load spring washer 100 may be introduced.

Figure 7A:
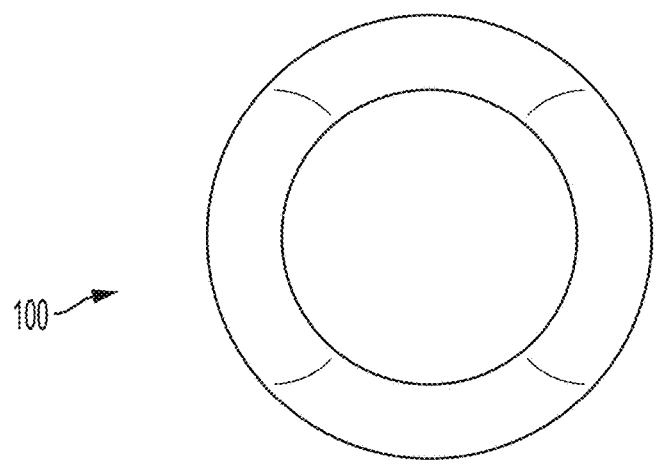
FIGS. 7A-7C show schematic images of a load spring washer according to non-limiting embodiments or aspects.
Figure 7B:
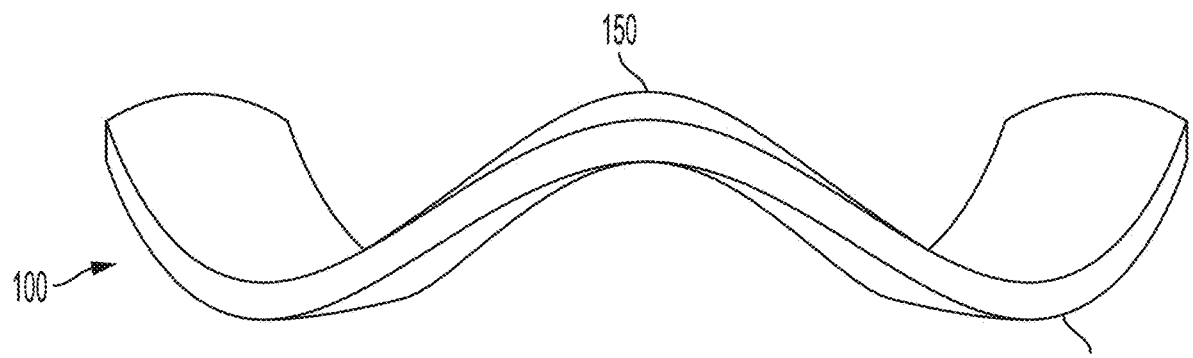
Figure 7C:
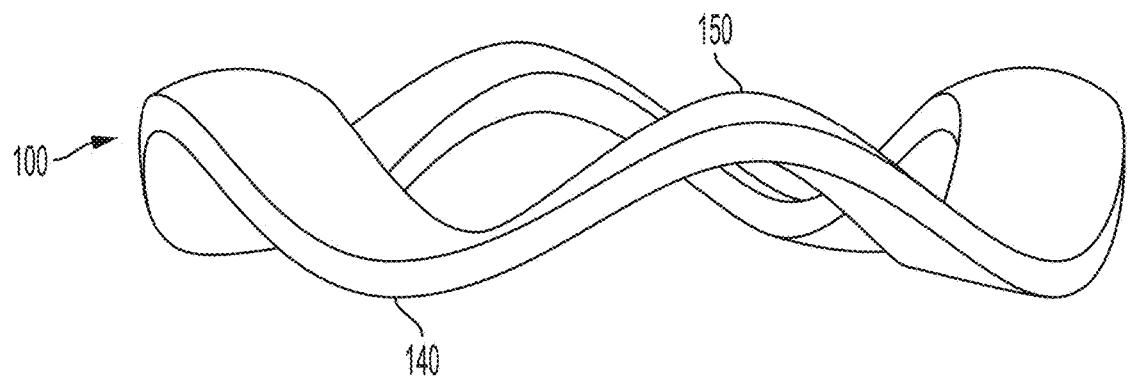
Figure 8A:
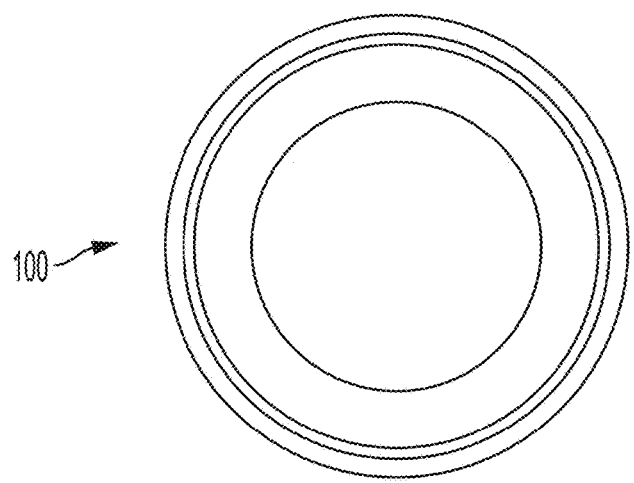
FIGS. 8A-8D show schematic images of a load spring washer according to non-limiting embodiments or aspects.
Figure 8B:
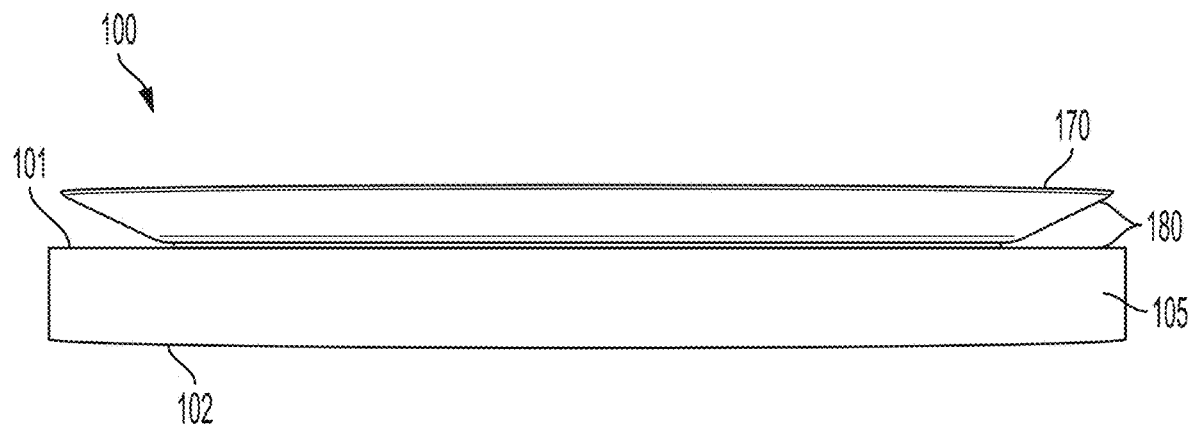
Figure 8C:
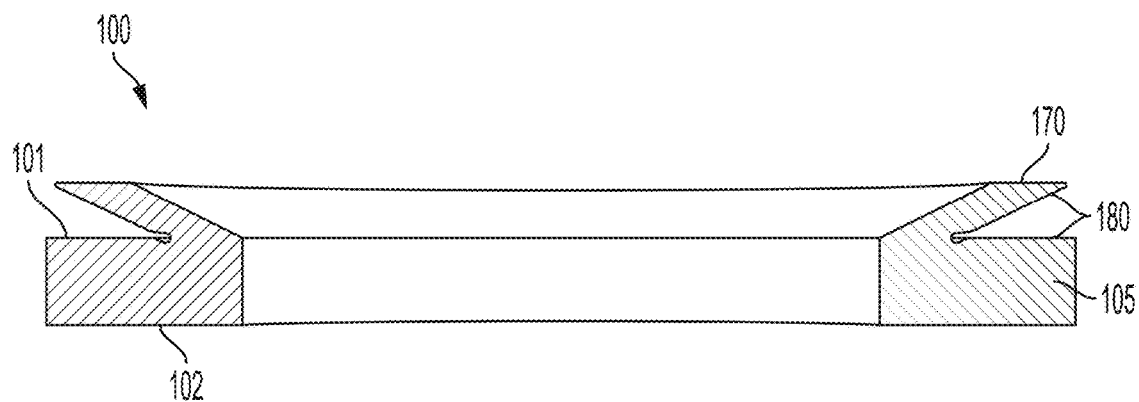
Figure 8D:
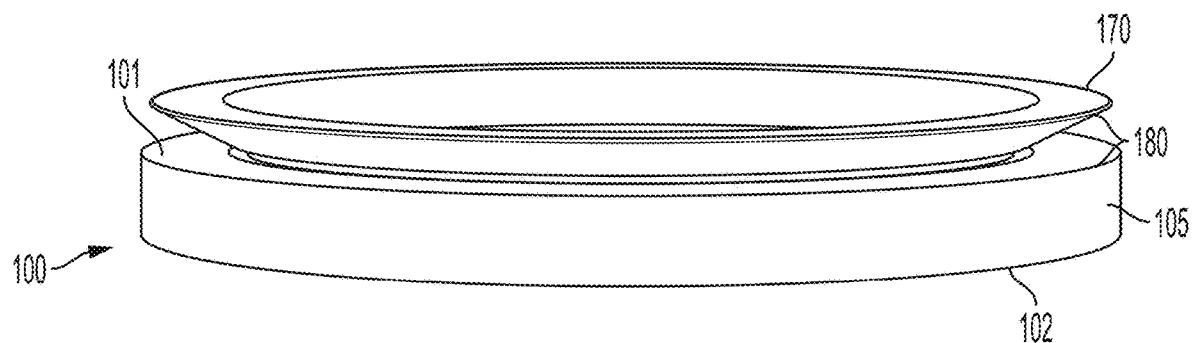

Turning to FIGS. 7A-7C, shown are schematic top (FIG. 7A) and side (FIGS. 7B-7C) views of a load spring washer 100 according to a non-limiting embodiment or aspect. In the illustrated non-limiting embodiment or aspect, load spring washer 100 has a wave shape. While FIGS. 7B-7C show a sine wave, including peaks 150 and troughs 140, it is to be understood that the present disclosure is not so limited, and various wave shapes, for example and without limitation square waves, sawtooth waves, and triangle waves, may be used, so long as the wave shape provides the desired buckling characteristics described herein. In addition, while not illustrated in FIGS. 7A-7C, in non-limiting embodiments or aspects the wave shape load spring washer 100 further includes one or more protrusions 110 as described herein.

Turning to FIGS. 8A-8D, shown are top (FIG. 8A), side (FIG. 8B), cross-sectional (FIG. 8C), and perspective (FIG. 8D) views of a load spring washer 100 according to a non-limiting embodiment or aspect. In the illustrated non-limiting embodiment or aspect, load spring washer 100 includes main body 105 and a frustoconical portion 170 at a proximal (uppermost) end of the main body 105. Frustoconical portion 170 may assume the orientation illustrated in FIGS. 8B-8C (larger circumference at the proximal end thereof) or an inverted orientation (larger circumference at the distal (bottommost) end thereof, not shown). In the illustrated non-limiting embodiment or aspect, where the portion of the frustoconical portion 170 having the larger circumference is arranged at the proximal (uppermost) end, gap 180 having a height is defined between proximal (uppermost) end of frustoconical portion 170 and proximal surface 101 of main body 105. In the illustrated non-limiting embodiment or aspect, proximal-most end of frustoconical portion 170 buckles towards the distal (bottommost) end of the load spring washer 100 when force is applied to the load spring washer 110 in a direction parallel to the longitudinal axis defined by proximal surface 101 and distal surface 102 of main body 105, such that the height of gap 180 is smaller than when no force is applied to the load spring washer 100.

Figure 9A:
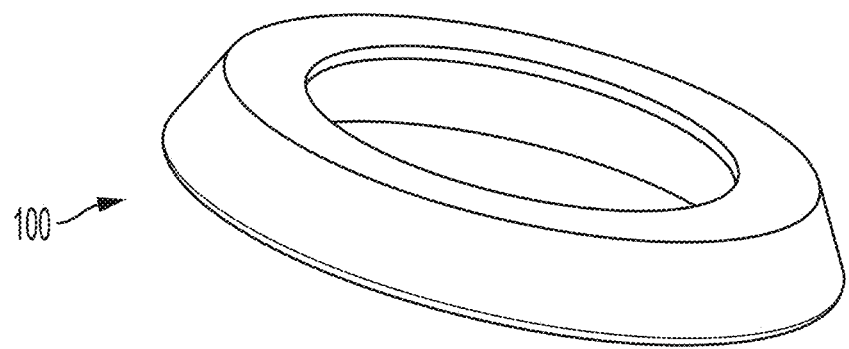
FIGS. 9A-9B show schematic images of a load spring washer according to non-limiting embodiments or aspects.
Figure 9B:
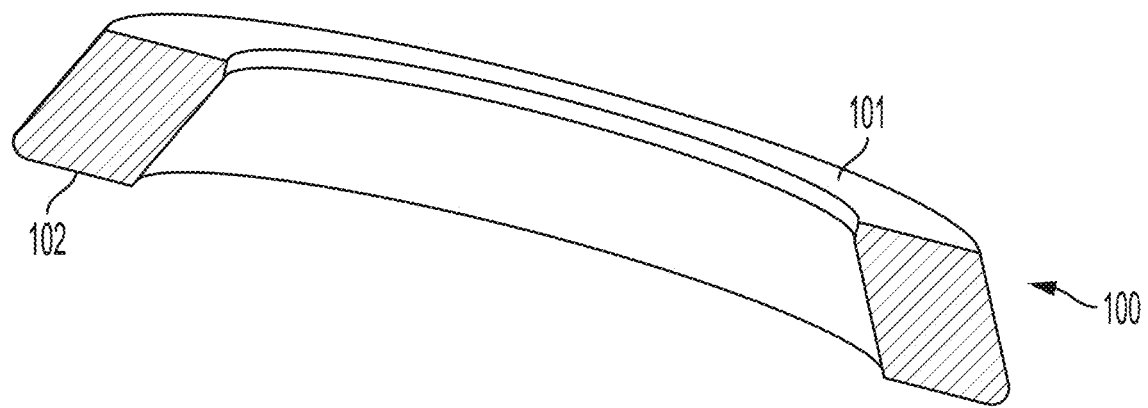

Turning to FIGS. 9A-9B, shown are perspective (FIG. 9A and cross-sectional (FIG. 9B) views of a load spring washer 100 according to a non-limiting embodiment or aspect. In the illustrated non-limiting embodiment or aspect, load spring washer 100 has a frustoconical shape, with proximal surface 101 being narrower (smaller circumference) than distal surface 102, though the opposite orientation may be employed. In the illustrated non-limiting embodiment or aspect, proximal surface 101 buckles towards the distal surface 102 of the load spring washer 100 when force is applied to the load spring washer 110 in a direction parallel to the longitudinal axis defined by proximal surface 101 and distal surface 102.

Figure 10A:
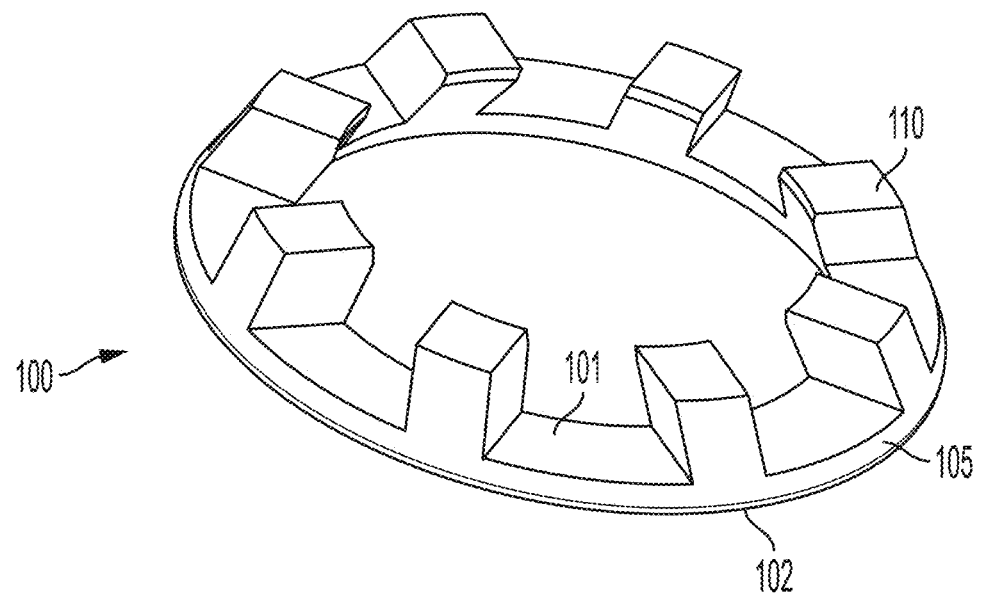
FIGS. 10A-10B show schematic images of a load spring washer according to non-limiting embodiments or aspects.
Figure 10B:
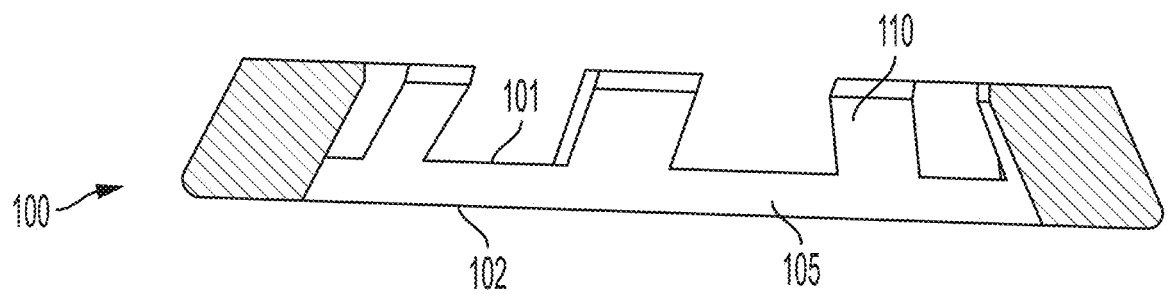

Turning to FIGS. 10A-10B, shown are perspective (FIG. 10A and cross-sectional (FIG. 10B) views of a load spring washer 100 according to a non-limiting embodiment or aspect. Load spring washer 100 illustrated in FIGS. 10A-10B includes protrusions 110. Protrusions 110 are oriented in such a manner that, as best illustrated in cross-sectional view in FIG. 10B, the protrusions, when considered with main body 105, provide a frustoconical shape to load spring washer 100. In the illustrated non-limiting embodiment or aspect, protrusions 110 buckle towards the distal surface 102 of the load spring washer 100 when force is applied to the load spring washer 110 in a direction parallel to the longitudinal axis defined by proximal surface 101 and distal surface 102 of main body 105.

Figure 12A:
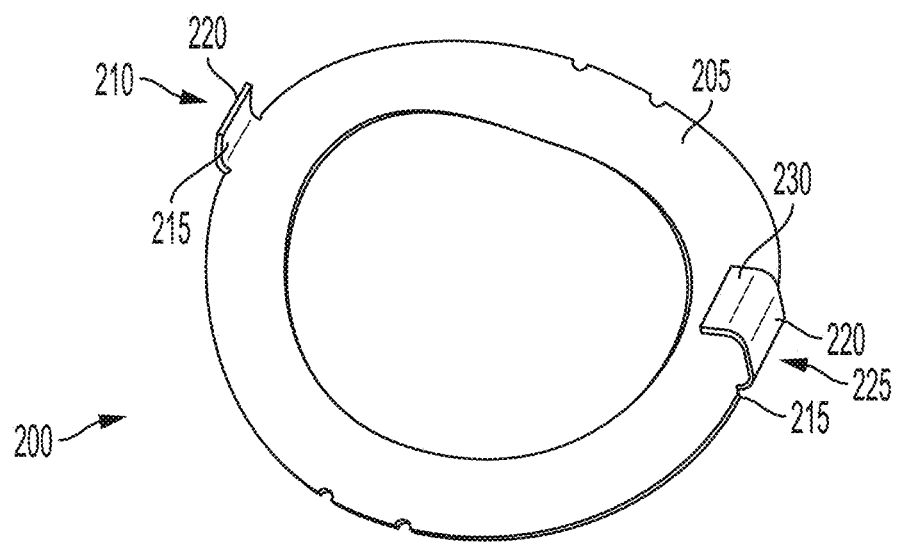
FIGS. 12A-12B show a load spring washer and placement of the same within the housing of a drug delivery device according to a non-limiting embodiment or aspect.
Figure 12B:
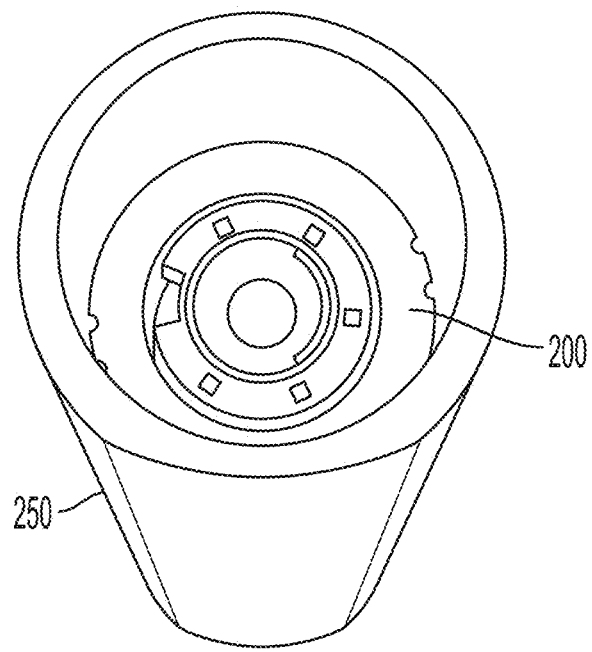

Turning to FIGS. 12A-12B, shown is a non-limiting embodiment or aspect of a load spring washer 200 including main body 205 and at least one flange 210 and/or at least one arm 225. FIG. 12B shows load spring washer 200 in a medical injection device housing 250. Flange 210 can be defined by a portion 215 extending outward from an outer diameter of main body 205, and a portion 220 extending substantially perpendicular to portion 215. The lengths of portions 215 and 220 can be adjusted based on the medical device into which the load spring washer 200 is introduced.

Arm 225 can include portion 215 extending outward from an outer diameter of main body 205, and a portion 220 extending substantially perpendicular to portion 215. Arm 225 further includes portion 230 extending substantially perpendicular to portion 220. In non-limiting embodiments or aspects, portion 230 is substantially parallel to portion 215.

Figure 13A:
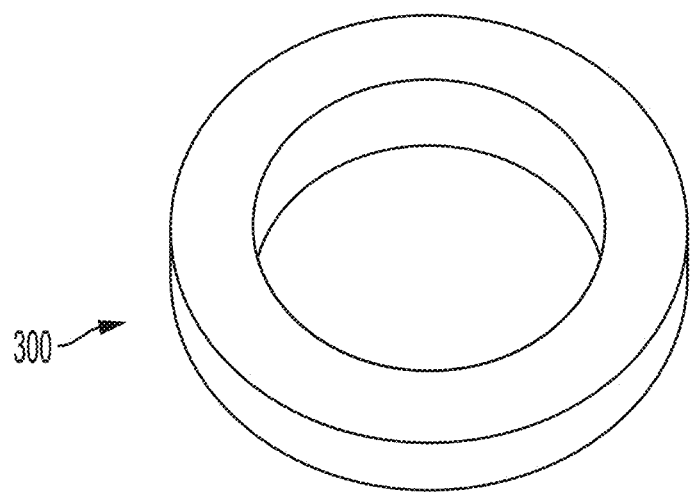
FIGS. 13A-13B show a load spring washer and placement of the same within the housing of a drug delivery device according to a non-limiting embodiment or aspect.
Figure 13B:
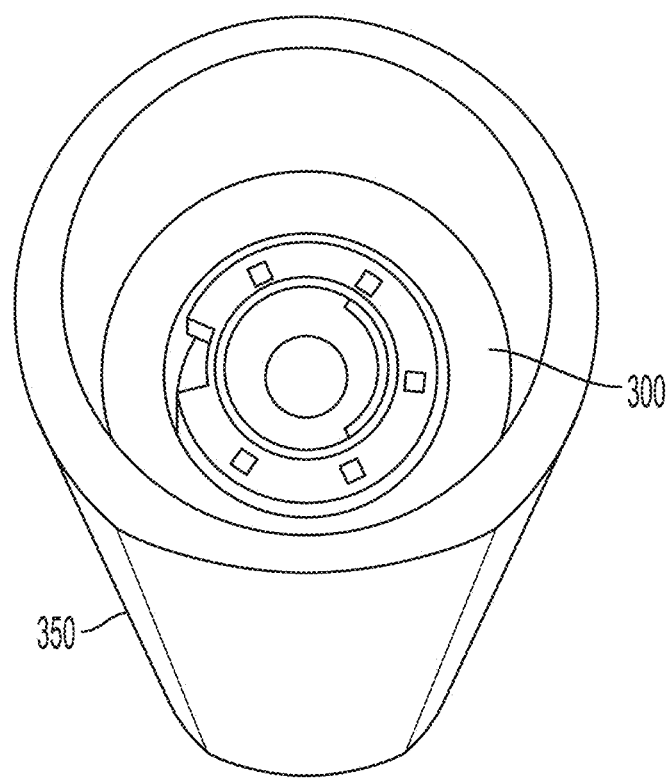

Turning to FIGS. 13A-13B, shown is a non-limiting embodiment or aspect of a load spring washer 300. FIG. 13B shows load spring washer 300 in a medical injection device housing 350. In the illustrated non-limiting embodiment or aspect, load spring washer 300 is a ring-shaped foam member.

Figure 14A:
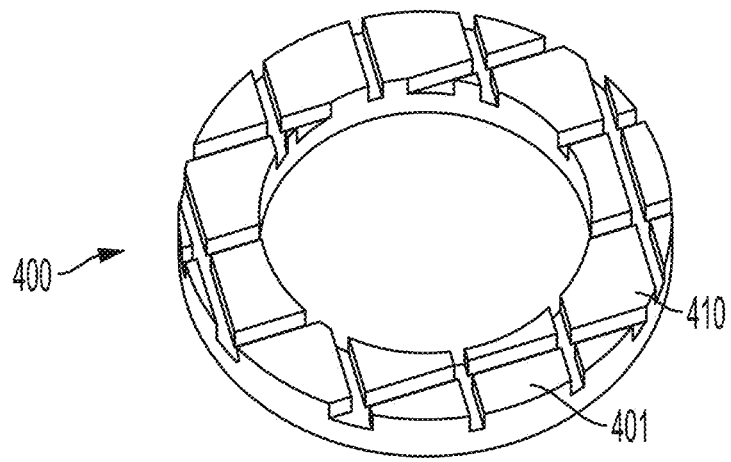
FIGS. 14A-14B show a load spring washer and placement of the same within the housing of a drug delivery device according to a non-limiting embodiment or aspect.
Figure 14B:
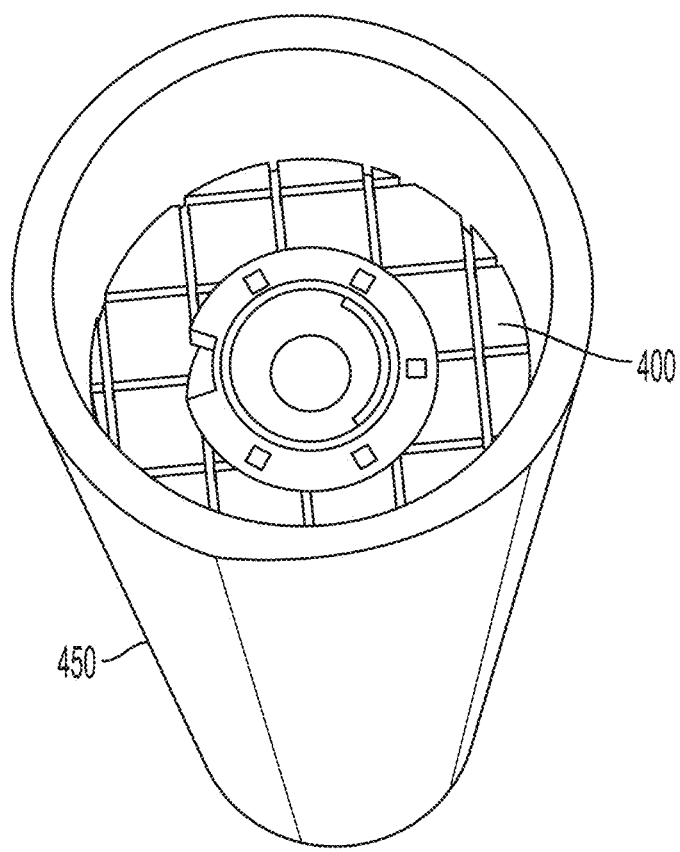

Turning to FIGS. 14A-14B, shown is a non-limiting embodiment or aspect of a load spring washer 400. FIG. 14B shows load spring washer 400 in a medical injection device housing 450. In the illustrated non-limiting embodiment or aspect, load spring washer 400 includes one or more protrusions 410 and/or patterns cut into proximal surface 401. In the illustrated non-limiting embodiment or aspect, load spring washer 400 is a ring-shaped rubber-based member. Without wishing to be bound by the theory, it is believed that the pattern allows for buckling of various portions of the load spring washer 400 as described herein.

Figure 15A:
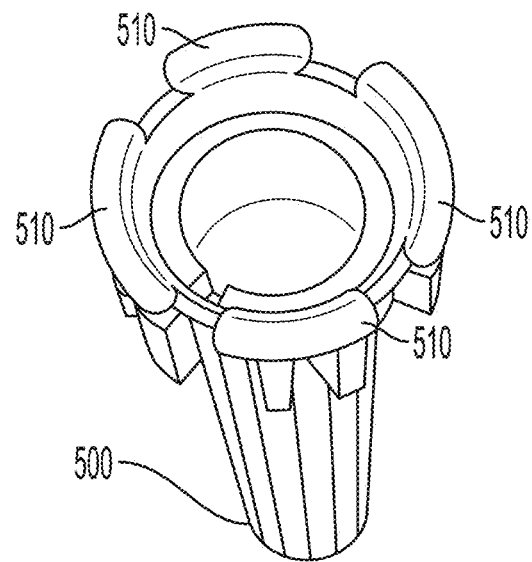
FIGS. 15A-15B show a load spring washer and placement of the same within the housing of a drug delivery device according to a non-limiting embodiment or aspect.
Figure 15B:
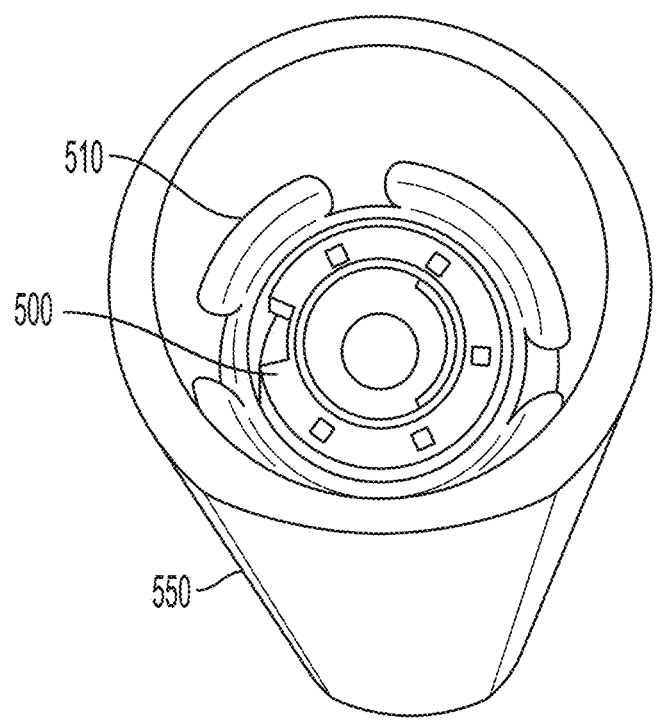

Turning to FIGS. 15A-15B, shown is a non-limiting embodiment where a load spring washer is not employed. Rather, the brake tower 500 of a medical injection device (described in greater detail below) includes one or more elastomeric protrusions 510 on a proximal surface thereof. Without wishing to be bound by the theory, it is believed that the elastomeric protrusions 510 allow for buckling as described herein. FIG. 15B shows brake tower 500 in a medical injection device housing 550.

Figure 16:
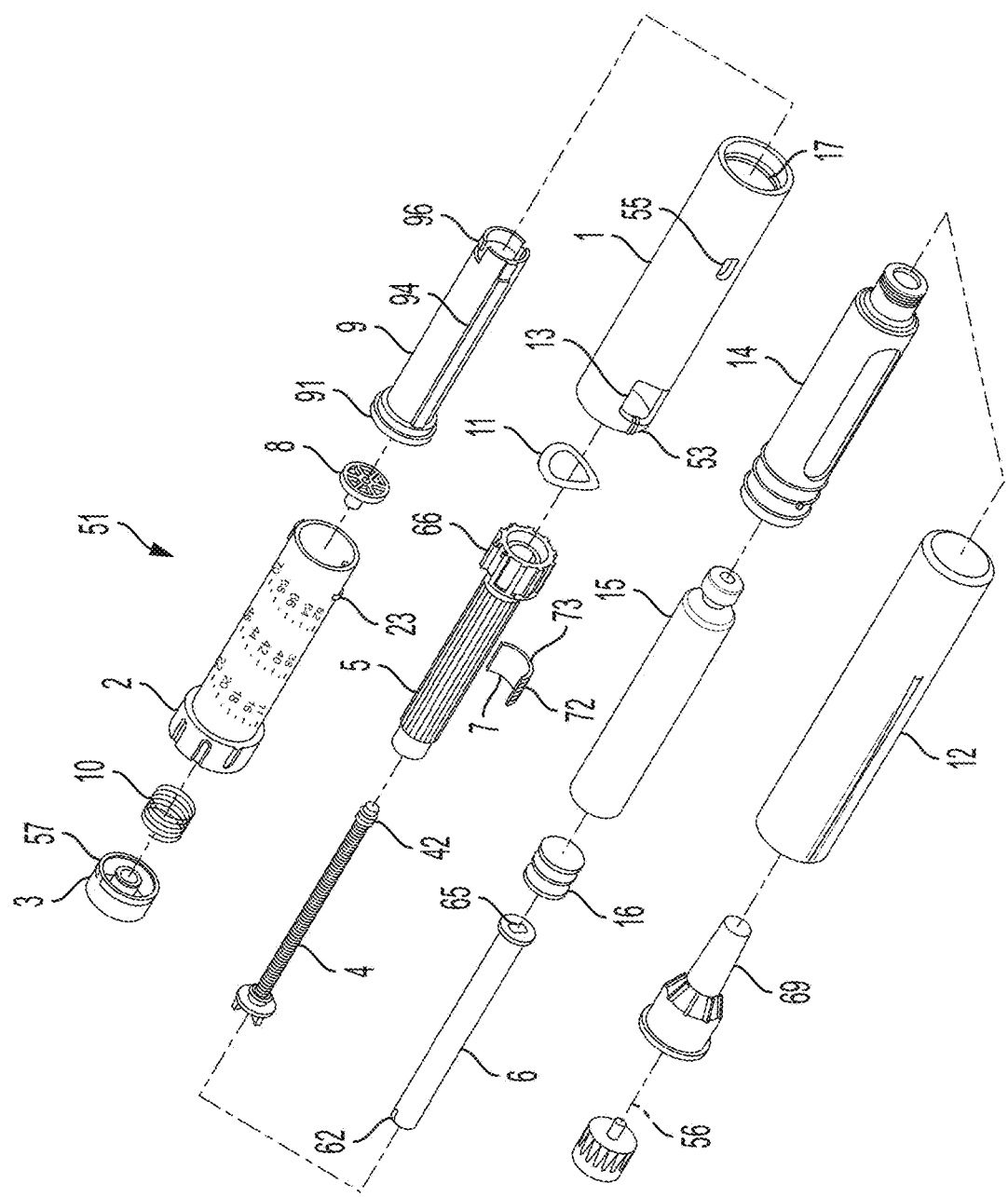
FIG. 16 is an exploded view of a medical injection device including a load spring washer as described herein.

Also provided herein is a medical injection device including a load spring washer as described above. Such devices, such as injection pens, are described in, for example and without limitation, U.S. Pat. No. 9,421,334, which is incorporated herein by reference in its entirety. With reference to FIG. 16, shown is an exploded view of an injection pen 51 for delivery of a composition to a user. As shown, the injection pen 51 includes a pen upper body or housing 1, which houses a plurality of dose setting and injection components. The pen upper body 1 is connected to a cartridge holder 14, which houses a medication cartridge 15. The injection pen 51 may also include a lower pen cap 12 to cover the cartridge 15 and cartridge holder 14 when the injection pen is not in use. As shown, the injection pen 51 can include a dose set knob 2 that includes a knob-like portion that is rotated by a user to set a desired dose. The dose set knob 2 can also include a plurality of numerals, corresponding to a number of dosage units that is visible through a window 13 provided on the pen upper body 1. A user rotates the dose set knob 2 until the desired dose is visible in the window 13. The pen upper body 1 can include an arrow or other indicator 53 to precisely indicate the set dose. Once the desired dose is set, a user presses the button 3 until the set dosage amount is completely injected. An outer shield 69 can cover a needle 56 to prevent accidental needle sticks upon removal of the lower pen cap 12.

Injection pen 51 includes a push button 3, provided at a proximal end, closest to a user and farthest from a needle 56, of the pen upper body 1. The push button 3 can include an annular bead or rim 57 that engages with a corresponding annular groove (not shown) provided on the internal surface of the dose set knob 2. The annular rim and groove connection can be a friction fit that maintains the push button 3 in a biased position on the dose set knob 2 under the force of a button spring 10, but allows the push button 3 to be pushed into the dose set knob 2 for injecting a set dose. The interior of the push button 3 can accommodate a setback bearing insert 8 that rests on an internal surface at a proximal end of a setback member or driver 9. The push button 3 can be designed to rotate freely on the setback bearing insert 8.

The setback member or driver 9 can be a cylindrical member, coaxial with and surrounded by the dose set knob 2. The setback member 9 can be provided co-axially around a brake tower 5 that is axially and rotatably fixed to the pen upper body 1. The brake tower 5 co-axially surrounds a piston rod 6. The piston rod 6 includes a set of keys 62 that engage a slot (not shown) internal to the brake tower 5 to rotatably lock the piston rod 6 to the brake tower 5. The piston rod 6 can include a plurality of threads (not shown) provided on the interior surface thereof. The piston rod 6 can co-axially surround a lead screw 4 that includes a series of threads 42 at least at its distal end. The lead screw threads 42 can be configured to be in threaded engagement with the internal threads (not shown) provided on the interior of piston rod 6. Due to its threaded engagement with the lead screw 4, the piston rod 6 can be moved into the cartridge 15 during injection to press on a stopper 16 provided inside the cartridge 15 to expel a dose of medication.

With reference to the present disclosure, injection pen 51 includes load spring washer 11, provided between a distal end of the brake tower 5 and the cartridge 15 and/or cartridge holder 14, to bias the cartridge 15 in a distal direction, thereby reducing/preventing movement of the cartridge 15. Reducing and/or preventing movement of the cartridge 15 can reduce rattling and improve needle 56 penetration into the cartridge 15 before priming.

Example

Load spring washers were formed out of a highly resilient elastomeric material including the following ingredients:

TABLE 1

| Ingredient | PHR | Density (g/ml) | Formulation Volume (ml) | Batch Weight (g) | Batch Weight (lbs) |
| --- | --- | --- | --- | --- | --- |
| KELTAN 9565Q | 150 (equivalent to 100 PHR of the polymer) | 0.87 | 172.4 | 1719 | 3.8 |
| MINSTRON Vapor | 37 | 2.80 | 13.2 | 424 | 0.9 |
| Mineral Oil | 10 | 0.87 | 11.5 | 115 | 0.3 |
| Zinc Oxide | 5 | 5.61 | 0.9 | 57 | 0.1 |
| Stearic Acid | 1 | 0.94 | 1.1 | 11 | 0.0 |
| SONGNOX 1076 | 2 | 0.90 | 2.2 | 23 | 0.1 |
| TBzTD | 2.5 | 1.40 | 1.8 | 29 | 0.1 |
| VULTAC710 | 6.5 | 0.80 | 8.1 | 75 | 0.2 |
| Sulfur/80 | 1 | 2.07 | 0.5 | 11 | 0.0 |

The above material was utilized to manufacture load spring washers of various orientations/shapes, as shown in FIG. 11. Data is shown presented in the tables below.

TABLE 2

| Sample | Compressive Load at Max Load (N) | Area Loading (mJ) | Area Unloading (mJ) |
| --- | --- | --- | --- |
| Ring (Cycle 1) | 21.070760 | 12.11671 | |
| Ring (Cycle 2) | 27.06701 | 16.34493 | |
| Ring (Cycle 3) | 28.86325 | 18.21729 | |
| Ring (Cycle 4) | 28.57111 | 18.33210 | |
| H-Shape (Cycle 1) | 39.58269 | 22.04388 | −19.03213 |
| H-Shape (Cycle 2) | 54.70945 | 34.01410 | |

TABLE 2-continued

| Sample | Compressive Load at Max Load (N) | Area Loading (mJ) | Area Unloading (mJ) |
|---|---|---|---|
| H-Shape (Cycle 3) | 55.12173 | 33.77259 | |
| Star-Shape 7 (Cycle 1) | 34.50593 | 18.54269 | |
| Star-Shape 7 (Cycle 2) | 36.79152 | 19.66360 | |
| Star-Shape 6 (Cycle 1) | 23.41913 | 10.59406 | −9.08724 |
| Star-Shape 6 (Cycle 2) | 37.52744 | 19.25595 | |
| Star Shape 5 (Cycle 1) | 20.81262 | 8.90632 | |
| Star Shape 5 (Cycle 2) | 35.15383 | 16.75382 | |
| Star-Shape 8 (Cycle 1) | 24.83673 | 10.29839 | |
| Star-Shape 8 (Cycle 2) | 46.02887 | 23.23951 | |
| Mean | 34.31326 | 18.80640 | −14.05969 |
| Standard Deviation | 11.00674 | 7.46342 | 7.03210 |

TABLE 3

| Sample | Compressive Load at 0.06 mm (N) | Compressive Load at 0.1 mm (N) | Area Loading-Unloading |
|---|---|---|---|
| Ring (Cycle 1) | 0.11229 | 0.12129 | |
| Ring (Cycle 2) | 0.12245 | 0.14109 | |
| Ring (Cycle 3) | 0.14285 | 0.18381 | |
| Ring (Cycle 4) | 0.14561 | 0.20023 | |
| H-Shape (Cycle 1) | 0.14093 | 0.16526 | 22.02485 |
| H-Shape (Cycle 2) | 0.37301 | 0.69075 | |
| H-Shape (Cycle 3) | 0.38491 | 0.72202 | |
| Star-Shape 7 (Cycle 1) | 0.21051 | 0.33861 | |
| Star-Shape 7 (Cycle 2) | 0.26773 | 0.38741 | |
| Star-Shape 6 (Cycle 1) | 0.12589 | 0.14490 | 10.58497 |
| Star-Shape 6 (Cycle 2) | 0.18198 | 0.27805 | |
| Star Shape 5 (Cycle 1) | 0.12710 | 0.16690 | |
| Star Shape 5 (Cycle 2) | 0.14909 | 0.18438 | |
| Star-Shape 8 (Cycle 1) | 0.13538 | 0.15526 | |
| Star-Shape 8 (Cycle 2) | 0.16724 | 0.22068 | |
| Mean | 0.18580 | 0.27358 | 16.30491 |
| Standard Deviation | 0.08791 | 0.19092 | 8.08921 |

Figure 17:
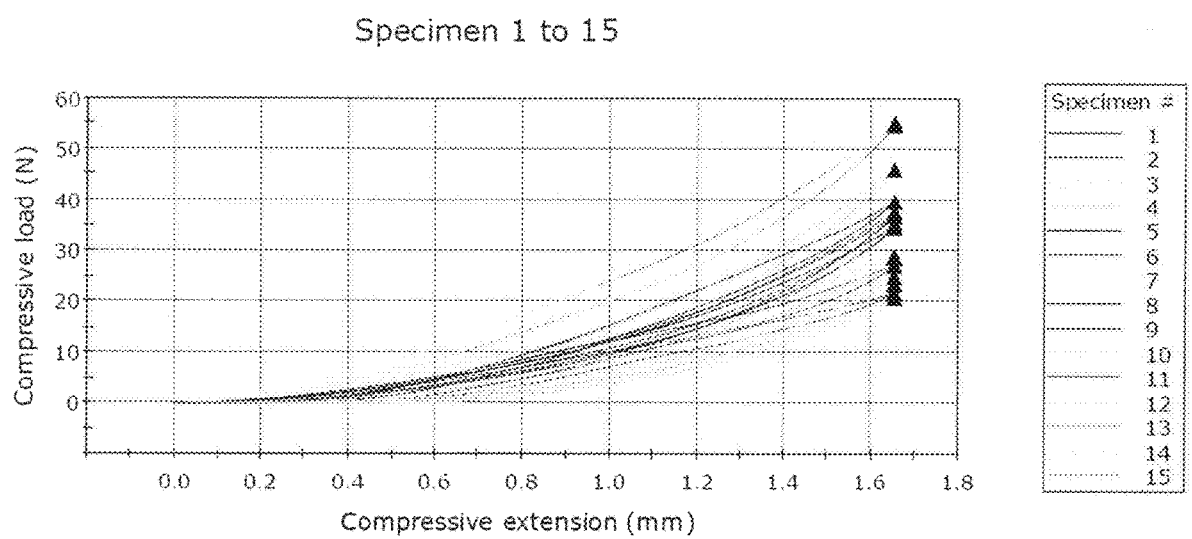
FIG. 17 is a graph showing load against extension for one non-limiting embodiment or aspect of a load spring washer described herein.

In addition, data (compressive load vs. compressive extension) from the above samples is presented in FIG. 17.

In addition, 19 more samples were produced from a silicone-based rubber material durometer Shore A 35 where the silicone rubber rings were cut using a 14 mm outer diameter cutting die and the internal diameter was subsequently punched with a 10 mm (samples 5, 6, and 7 on Tables 4 and 5) or 12 mm (otherwise) cutting dies. The rings were cut from ASTM rubber plates 6.5" L×6.5" W and 1.8-2.0 mm thick. All samples in Tables 4 and 5 are the same test but with the forces specified at different compression distance. The maximum compression extension was 1.5 mm Tables 6 and 7 are the same test but with the forces specified at different compression distance. The maximum compression extension was 1.5 mm.

Figure 18A:
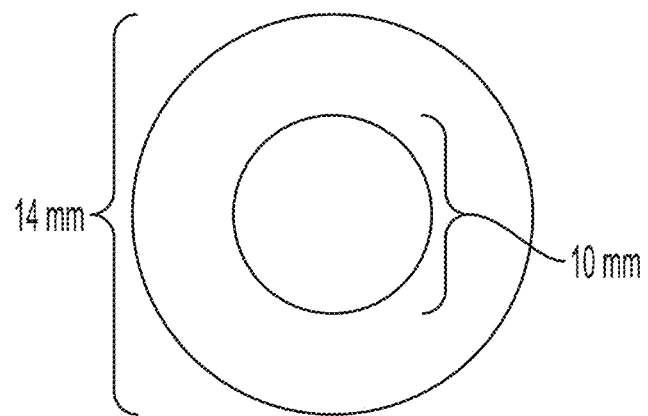
FIGS. 18A-18B are schematic images of a load spring washer according to non-limiting embodiments or aspects.
Figure 18B:
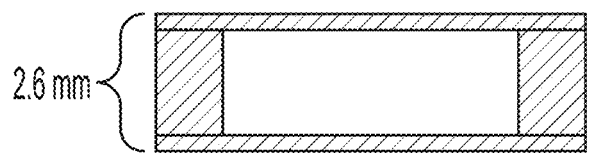

All samples for Tables 4 and 5, 6 and 7 were made in the same way, by punching rings from a rubber slab, with dimensions as provided in FIGS. 18A-18B (FIG. 18A is a top view, FIG. 18B is a cross-sectional view), with data presented below:

TABLE 4

| Sample | Compressive Load at Max Load (N) | Area Loading (mJ) |
|---|---|---|
| 1 | 93.88897 | 0.18077 |
| 2 | 10.45748 | 0.03745 |
| 3 | 16.52684 | 0.04315 |
| 4 | 10.11987 | 0.03775 |
| 5 | 95.78949 | 0.12344 |
| 6 | 83.01142 | 0.06146 |

TABLE 4-continued

| Sample | Compressive Load at Max Load (N) | Area Loading (mJ) |
|---|---|---|
| 7 | 84.12963 | 0.06087 |
| 8 | 47.08079 | 0.04381 |
| 9 | 60.84618 | 0.05374 |
| 10 | 51.33612 | 0.04990 |
| 11 | 34.94950 | 0.04530 |
| 12 | 34.81499 | 0.03465 |
| 13 | 56.72254 | 0.03722 |
| 14 | 62.92496 | 0.03778 |
| 15 | 50.73323 | 0.06551 |
| 16 | 46.06429 | 0.07922 |
| 17 | 34.00679 | 0.08139 |
| 18 | 27.50728 | 0.05415 |
| 19 | 24.93059 | 0.03774 |
| Mean | 48.72847 | 0.06133 |
| Standard Deviation | 26.58819 | 0.03616 |

TABLE 5

| Sample | Compressive Load at 0.06 mm (N) | Compressive Load at 0.1 mm (N) |
|---|---|---|
| 1 | 2.05477 | 4.63418 |
| 2 | 0.46023 | 0.70048 |
| 3 | 0.507741 | 0.75857 |
| 4 | 0.44663 | 0.69240 |
| 5 | 1.43243 | 3.13971 |
| 6 | 0.72140 | 1.35426 |
| 7 | 0.72024 | 1.31258 |
| 8 | 0.50808 | 0.95933 |
| 9 | 0.61815 | 1.16032 |

TABLE 5-continued

| Sample | Compressive Load at 0.06 mm (N) | Compressive Load at 0.1 mm (N) |
|---|---|---|
| 10 | 0.58744 | 1.06286 |
| 11 | 0.53254 | 0.92751 |
| 12 | 0.41074 | 0.63211 |
| 13 | 0.43921 | 0.68218 |
| 14 | 0.44336 | 0.71033 |
| 15 | 0.71995 | 1.71387 |
| 16 | 0.91263 | 1.96137 |
| 17 | 0.95401 | 1.95577 |
| 18 | 0.61690 | 1.30184 |
| 19 | 0.41083 | 0.88197 |
| Mean | 0.71038 | 1.39693 |
| Standard Deviation | 0.41041 | 1.00186 |

Figure 19A:
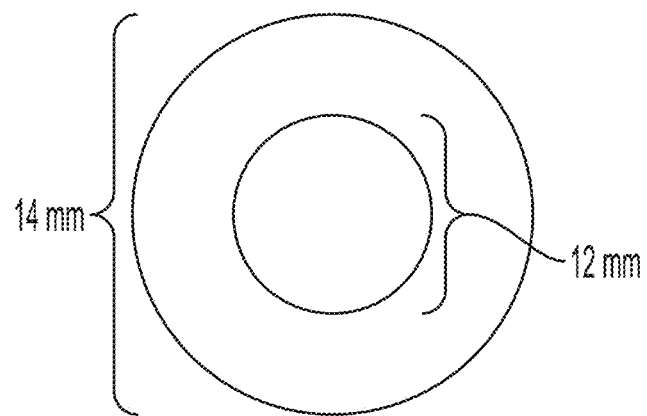
FIGS. 19A-19B are schematic images of a load spring washer according to non-limiting embodiments or aspects.
Figure 19B:
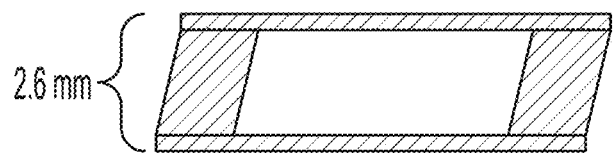

Lastly, 14 additional samples were produced with dimensions as provided in FIGS. 19A-19B (FIG. 19A is a top view, FIG. 19B is a cross-sectional view), with data presented below:

TABLE 6

| Sample | Compressive Load at Max Load (N) | Area Loading (mJ) |
|---|---|---|
| 1 | 24.69491 | 0.04113 |
| 2 | 37.05007 | 0.04490 |
| 3 | 33.01292 | 0.05191 |
| 4 | 37.35841 | 0.02748 |
| 5 | 34.43204 | 0.02544 |
| 6 | 47.63247 | 0.04586 |
| 7 | 41.19097 | 0.01437 |
| 8 | 41.629663 | 0.08237 |
| 9 | 21.41265 | 0.10109 |
| 10 | 17.45964 | 0.04048 |
| 11 | 43.15011 | 0.05729 |
| 12 | 38.22097 | 0.06700 |
| 13 | 30.09437 | 0.07706 |
| 14 | 26.62738 | 0.05819 |
| Mean | 33.85475 | 0.05247 |
| Standard Deviation | 8.80111 | 0.02371 |

TABLE 7

| Sample | Compressive Load at 0.06 mm (N) | Compressive Load at 0.1 mm (N) |
|---|---|---|
| 1 | 0.45692 | 1.02958 |
| 2 | 0.48036 | 1.30489 |
| 3 | 0.56545 | 1.37173 |
| 4 | 0.30807 | 0.57717 |
| 5 | 0.28093 | 0.54226 |
| 6 | 0.50611 | 1.24077 |
| 7 | 0.14521 | 0.31382 |
| 8 | 0.96456 | 2.14320 |
| 9 | 1.18252 | 2.40098 |
| 10 | 0.43440 | 1.05093 |
| 11 | 0.65224 | 1.42832 |
| 12 | 0.76420 | 1.74184 |
| 13 | 0.85138 | 2.07813 |
| 14 | 0.66296 | 1.38261 |
| Mean | 0.58966 | 1.32902 |
| Standard Deviation | 0.28198 | 0.61696 |

The rings tested in Table 4 and 5 and 6 and 8 performed as expected showing different orders of buckling and limiting the developed forces for compression extension up to 1.5 mm below. The variations on the max compressions forces is due to either the width of the ring 1.5 mm on samples 5, 6, and 7 on Tables 4 and 5 or the variation on the punching and centering of the dies during the ring manufacturing. In fact, the variability of the process created asymmetric cross sections of the rings which facilitate the buckling concept approach.

Although the devices have been described in detail for the purpose of illustration based on what is currently considered to be the most practical and preferred embodiments, it is to be understood that such detail is solely for that purpose and that the systems and methods are not limited to the disclosed embodiments, but on the contrary, is intended to cover modifications and equivalent arrangements that are within the spirit and scope of the appended claims. For example, it is to be understood that the present systems and methods contemplate that, to the extent possible, one or more features of any embodiment can be combined with one or more features of any other embodiment.

The invention claimed is:

1. A medical injection device comprising:
a housing having a proximal end, a distal end, and sidewall therebetween defining an interior;
a brake member received within the interior of the housing;
a cartridge holder received within the interior of the housing, distal of the brake member;
a cartridge received within the cartridge holder and holding a composition therein;
a load spring washer comprised of an elastomeric material and comprising:
a main body comprising a plurality of concentric rings with a gap therebetween, at least one of the plurality of concentric rings having a diameter smaller than another of the plurality of concentric rings and each of the plurality of concentric rings having a proximal surface and a distal surface; and
one or more protrusions extending proximally away from the proximal surface of the main body, one of at least one of the plurality of concentric rings, the load spring washer received within the interior of the housing and positioned between the brake member and the cartridge holder such that, when the medical injection device is assembled, the one or more protrusions abuts the brake member and the distal surface abuts the cartridge and/or the cartridge holder;
an injection needle in fluid communication with the cartridge and arranged at a distal end of the housing; and
an actuation member arranged at the proximal end of the housing, the actuation member configured to actuate the medical injection device to deliver the composition through the injection needle.

2. The medical injection device of claim 1, wherein a cross-sectional profile of the one or more protrusions of the load spring washer, taken along a plane extending between the proximal surface and the distal surface, comprises a parallelogram.

3. The medical injection device of claim 1, wherein at least one of the concentric rings has a width that is greater than a width of another of the concentric rings.

4. The medical injection device of claim 1, wherein a cross-sectional profile of the one or more protrusions of the load spring washer, taken along a plane extending between the proximal surface and the distal surface, comprises a u-shape, wherein the u-shape comprises:
a first arm connected to a first of the plurality of concentric rings of the main body and a second arm connected to a second of the plurality of concentric rings of the main body, both the first arm and the second arm extending parallel to a longitudinal axis defined by the proximal surface and the distal surface of the main body; and a cross-member connected to the first arm and the second arm and extending perpendicular to the longitudinal axis defined by the proximal surface and the distal surface of the main body.

5. The medical injection device of claim 1, wherein the one or more protrusions of the load spring washer comprise an arch comprising:

a first arm connected to a first of the plurality of concentric rings of the main body and a second arm connected to a second of the plurality of concentric rings of the main body, both the first arm and the second arm extending parallel to a longitudinal axis defined by the proximal surface and the distal surface of the main body; and a curved portion connected to the first arm and the second arm.

6. The medical injection device of claim 1, wherein the load spring washer comprises an ethylene propylene diene monomer rubber.

7. The medical injection device of claim 1, wherein the load spring washer has a Shore A hardness of 20-40.

8. The medical injection device of claim 1, wherein the plurality of concentric rings each comprise an outer diameter and an inner diameter, wherein the outer diameter is substantially circular and comprises two opposed semi-circular cut-out portions, and the inner diameter is circular.

9. The medical injection device of claim 1, wherein the main body of the load spring washer is a star shape, such that the proximal surface and the distal surface comprise a plurality of sloping surfaces forming plateaus, wherein the plateaus are parallel to a plane extending between the proximal surface and the distal surface, and the proximal surface and distal surface mirror each other across the plane.

* * * * *